United States Patent
Kinkade

(10) Patent No.: US 10,226,375 B2
(45) Date of Patent: Mar. 12, 2019

(54) URINARY INCONTINENCE PAD

(71) Applicant: Darla Kinkade, Eugene, OR (US)

(72) Inventor: Darla Kinkade, Eugene, OR (US)

( * ) Notice: Subject to any disclaimer, the term of this patent is extended or adjusted under 35 U.S.C. 154(b) by 349 days.

(21) Appl. No.: 15/045,955

(22) Filed: Feb. 17, 2016

(65) Prior Publication Data

US 2016/0317362 A1    Nov. 3, 2016

Related U.S. Application Data

(60) Provisional application No. 62/155,601, filed on May 1, 2015.

(51) Int. Cl.
| | | |
|---|---|---|
| *A61F 5/455* | (2006.01) | |
| *A61F 5/44* | (2006.01) | |
| *A61F 13/472* | (2006.01) | |

(52) U.S. Cl.
CPC .......... *A61F 5/4401* (2013.01); *A61F 13/472* (2013.01)

(58) Field of Classification Search
CPC ............ A61F 13/82; A61F 2013/15121; A61F 13/471; A61F 5/453
USPC ..................... 604/349–350, 385.03
See application file for complete search history.

(56) References Cited

U.S. PATENT DOCUMENTS

| | | | |
|---|---|---|---|
| 4,590,931 A * | 5/1986 | Kidwell, Jr. ............. | A61F 5/40 128/DIG. 15 |
| 4,595,392 A | 6/1986 | Johnson et al. | |
| 4,971,074 A * | 11/1990 | Hrubetz ................ | A61F 2/0054 128/885 |
| 5,057,096 A | 10/1991 | Faglione | |
| 5,916,205 A | 6/1999 | Olson et al. | |
| 6,392,117 B1 | 5/2002 | Mayer et al. | |
| 6,890,325 B2 | 5/2005 | Edens et al. | |
| 8,328,781 B2 | 12/2012 | Mizutani et al. | |

* cited by examiner

*Primary Examiner* — Susan S Su
(74) *Attorney, Agent, or Firm* — Global Intellectual Property Agency, LLC; Daniel Boudwin

(57) ABSTRACT

A urinary incontinence pad for females. The urinary incontinence pad includes an absorbent, tubular pad having a hollow interior. The pad includes a rounded first end and an open second end, wherein the rounded end serves as a barrier against the clitoris of a female user so as to prevent the pad from sliding when worn. The urinary incontinence pad further includes a channel that extends from the second end of the pad towards the first end thereof. The sides of the channel are flexible and biased towards one another so as to removably secure the pad to the labia of a user. In operation, the pad is removably secured between the labia majora and labia minora, wherein the channel is positioned facing the urethral meatus so as to absorb urine within the interior of the pad.

18 Claims, 3 Drawing Sheets

URINARY INCONTINENCE PAD

CROSS REFERENCE TO RELATED APPLICATION

This application claims the benefit of U.S. Provisional Application No. 62/155,601 filed on May 1, 2015. The above identified patent application is herein incorporated by reference in its entirety to provide continuity of disclosure.

BACKGROUND OF THE INVENTION

The present invention relates to urinary incontinence pads. More specifically, the present invention provides a urinary incontinence pad having a tubular shape that removably secures between the labia minora and labia majora of a female user.

Many women suffer from urinary incontinence, which often leads to wet undergarments and wet clothing. Such individuals choose to wear an incontinence pad in order to prevent embarrassment from clothes becoming wet while in public or around friends and family. However, conventional incontinence pads are uncomfortable, bulky, and visible underneath tighter fitting clothes. As a result, an individual becomes self-conscious and may be unwilling to go in public for fear of the incontinence pad being noticed or fear of having a leak occur. Therefore, there exists a need for a discrete urinary incontinence pad for females.

Devices have been disclosed in the prior art that relate to urinary incontinence pads. These include devices that have been patented and published in patent application publications. These devices generally relate to incontinence pads for females, such as U.S. Pat. No. 8,328,781, U.S. Pat. No. 4,595,392, U.S. Pat. No. 5,916,205, U.S. Pat. No. 5,057,096, U.S. Pat. No. 6,392,117, and U.S. Pat. No. 6,890,325.

These prior art devices have several known drawbacks. Such devices include a pad that can be placed between the folds of the labia in order to collect urine. However, these devices fail to provide a tubular pad having a rounded end in order to prevent the pad from sliding out of position while in use.

In light of the devices disclosed in the prior art, it is submitted that the present invention substantially diverges in design elements from the prior art and consequently it is clear that there is a need in the art for an improvement to existing urinary incontinence pads. In this regard the instant invention substantially fulfills these needs.

SUMMARY OF THE INVENTION

In view of the foregoing disadvantages inherent in the known types of urinary incontinence pads now present in the prior art, the present invention provides a new urinary incontinence pad wherein the same can be utilized for providing convenience for the user when discretely absorbing urine due to female incontinence.

It is therefore an object of the present invention to provide a new and improved urinary incontinence pad that has all of the advantages of the prior art and none of the disadvantages. The urinary incontinence pad comprises an absorbent, tubular pad having a hollow interior. The pad includes a rounded first end and an open second end, wherein the rounded end serves as a barrier against the clitoris of a female user so as to prevent the pad from sliding when worn. The urinary incontinence pad further includes a channel that extends from the second end of the pad towards the first end thereof. The sides of the channel are flexible and biased towards one another so as to removably secure the pad to the labia of a user. In operation, the pad is removably secured between the labia majora and labia minora, wherein the channel is positioned facing the urethral meatus so as to absorb urine within the interior of the pad.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
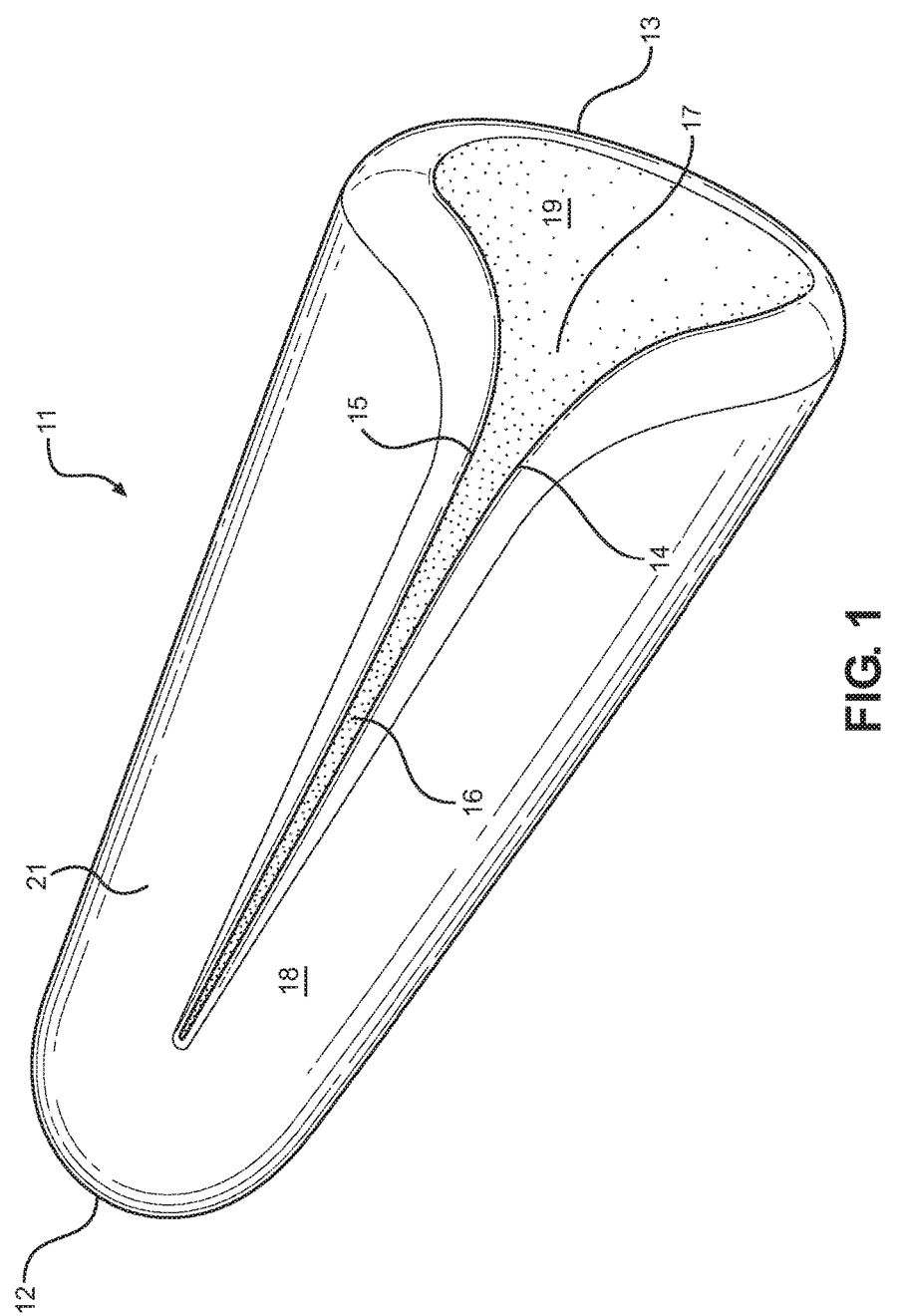
FIG. 1 shows a perspective view of the urinary incontinence pad.

Reference is made herein to the attached drawings. Like reference numerals are used throughout the drawings to depict like or similar elements of the urinary incontinence pad. For the purposes of presenting a brief and clear description of the present invention, the preferred embodiment will be discussed as used for absorbing urine due to female incontinence. The figures are intended for representative purposes only and should not be considered to be limiting in any respect.

Figure 2:
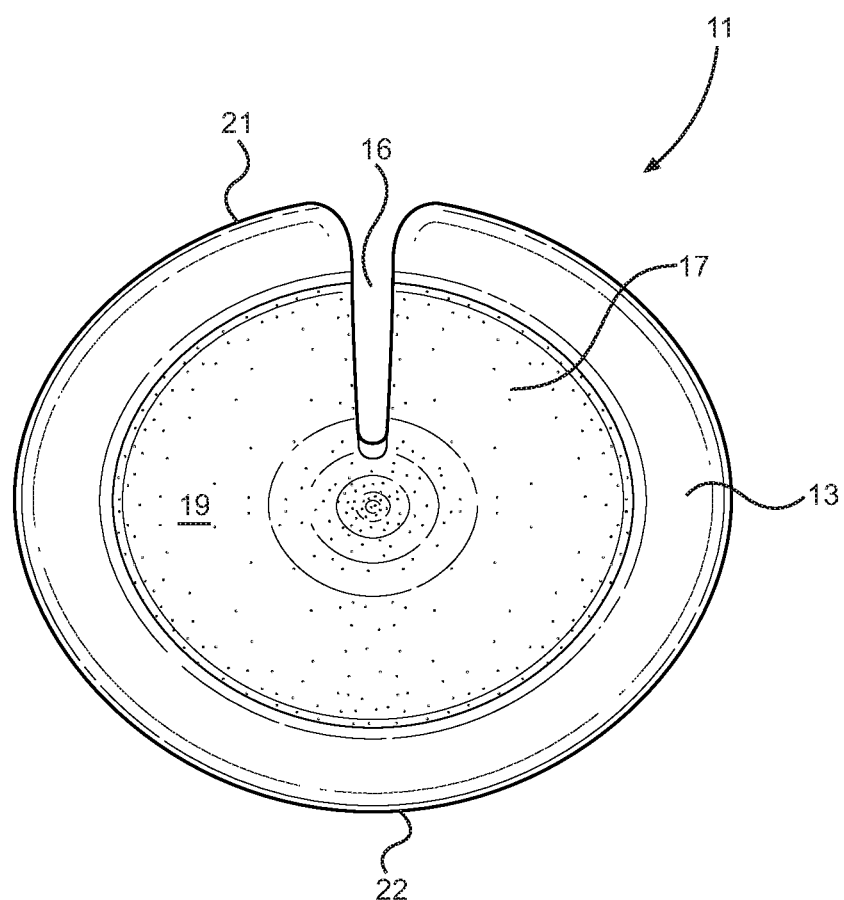
FIG. 2 shows a top down view of the urinary incontinence pad.

Referring now to FIGS. 1 and 2, there is shown a perspective view and a top down view of the urinary incontinence pad. The urinary incontinence pad 11 is adapted to provide a compact, discrete pad configured to be removably secured between the labia minora and labia majora of female user. The pad 11 is configured to absorb urine released from the urethral meatus as a result of bodily actions, such as sneezing, laughter, coughing, among other sudden and abrupt bodily movements. The pad 11 comprises an interior surface 19 and an exterior surface 18, wherein the interior surface 19 is adapted to be positioned against the user's body. The interior surface 19 of the pad 11 is composed of one or more layers of any suitable absorbent material, such as cotton or rayon. The urinary incontinence pad 11 is further adapted to prevent leakage therefrom via the exterior surface 18 composition. Preferably, the exterior surface 18 of the pad 11 comprises a layer composed of a liquid impermeable material to prevent leakage and seepage therethrough.

The urinary incontinence pad 11 is tubular and comprises a closed first end 12, an open second end 13, and a hollow interior volume 17 extending therebetween. Preferably, the pad 11 is tapered towards the first end 12, such that it is wider near the second end 13 in order to correspond to the shape of a labia. In the illustrated embodiment, a rear side 22 of the pad 11 is configured to contour to the shape of any undergarments worn so as to prevent obstruction and visibility through clothing.

On a front side 21 of the pad 11, a channel 16 extends from the open second end 13 of the pad 11 towards the closed first end 12 thereof. In the illustrated embodiment, the channel 16 is also tapered towards the first end 12 so as to correspond to the shape of the labia. The channel 16 comprises a first side 14 and a second side 15 that are semi-rigid and pliable so as to remain biased towards one another in order to allow the channel 16 to receive the labia minora within the interior volume 17 of the pad 11. The sides 14, 15 of the channel 16 are adapted to fit between the labia minora and the labia majora so as to removably secure the pad 11 to the user.

The first end 12 of the pad 11 is adapted to be positioned over the clitoris and the urethral meatus of a female user so as to absorb urine therefrom. Further, the first end 12 of the pad 11 comprises a rounded tip so as to prevent the pad 11 from sliding out of position once secured to a user. The first end 12 is adapted to serve as a barrier against the clitoris, thus preventing the pad 11 from moving backwards, towards a rear side of the user, and, therefore, falling off of the labia when worn. The second end 13 of the pad 11 is open so as to allow the channel 16 to be manually widened in order to receive the labia minora therein.

Figure 3:
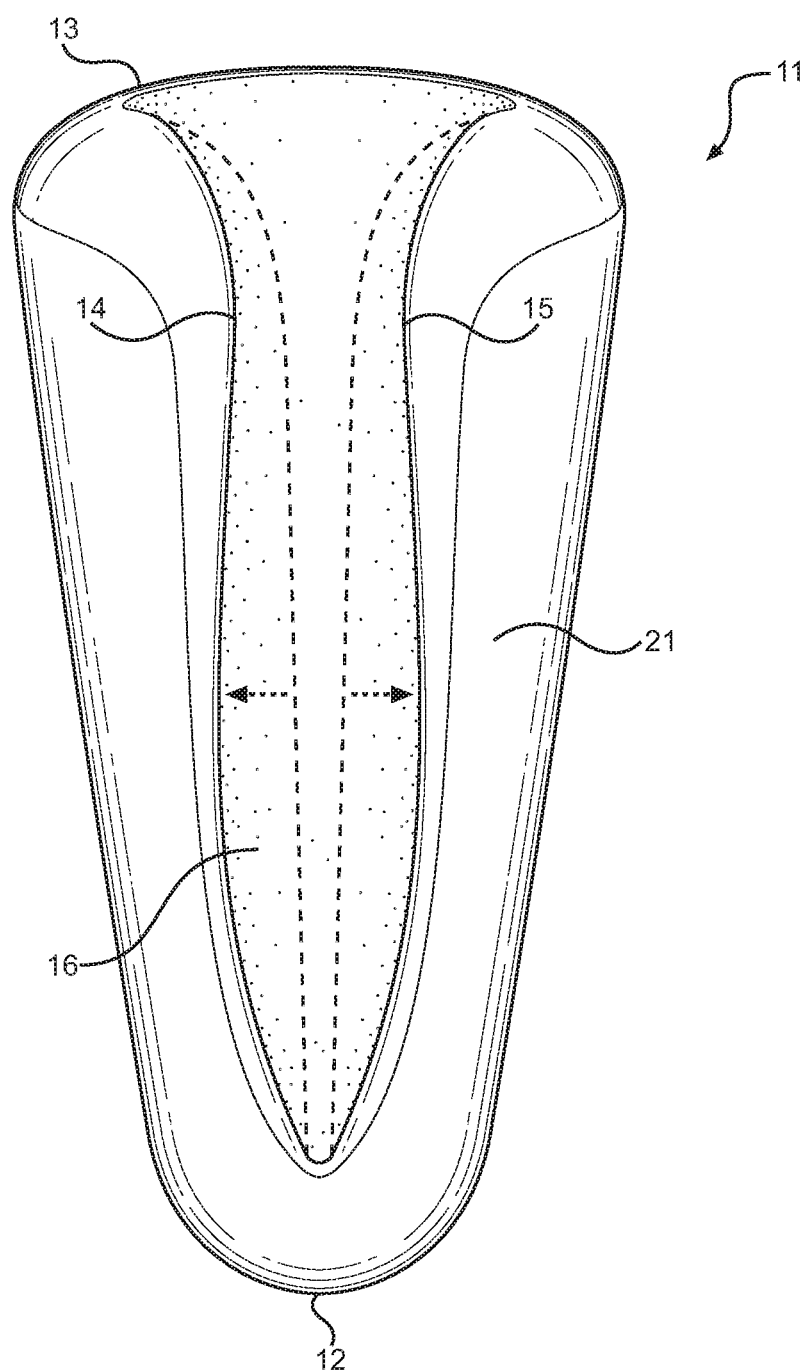
FIG. 3 shows a front view of the urinary incontinence pad.

Referring now to FIG. 3, there is shown a front view of the urinary incontinence pad. In operation, a user spreads the sides 14, 15 of the channel 16 apart and places the channel 16 over her labia minora, such that the sides 14, 15 are positioned between the labia minora and labia majora. The open second end 13 is positioned nearest to the rear side of a user's body and the first end 12 prevents the pad 11 from sliding beyond the clitoris. Once the channel 16 is in position, the user releases the sides 14, 15 thereof, wherein the sides move towards one another. The size of the channel 16 is adapted to allow the pad 11 to remain on the user. The front side 21 of the pad 11 is positioned so as to face the urethral meatus in order to absorb urine within the interior of the pad 11.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A urinary incontinence pad, comprising:
   a tubular pad having a closed first end, an open second end, and a hollow interior volume extending therebetween;
   a channel disposed on a front side of the tubular pad, wherein the channel extends from the open second end toward the closed first end;
   wherein the channel comprises a first side and a second side, wherein the first and second sides are biased toward each other;
   wherein the first and second sides are configured to removably secure between a labia minora and a labia majora when in use.

2. A urinary incontinence pad, comprising:
   a tubular pad having a closed first end, an open second end, and a hollow interior volume extending therebetween;
   a channel disposed on a front side of the tubular pad, wherein the channel extends from the open second end toward the closed first end;
   wherein the channel comprises a first side and a second side, wherein the first and second sides are biased toward each other;
   wherein the channel is dimensioned to correspond to a shape of a labia minora and a labia majora.

3. A urinary incontinence pad, comprising:
   a tubular pad having a closed first end, an open second end, and a hollow interior volume extending therebetween;
   a channel disposed on a front side of the tubular pad, wherein the channel extends from the open second end toward the closed first end;
   wherein the channel comprises a first side and a second side, wherein the first and second sides are biased toward each other;
   wherein the channel is tapered toward the closed first end of the tubular pad;
   wherein a tapered end of the channel is configured to secure about a clitoris of a user when in use.

4. A method of using a urinary incontinence pad, comprising:
   providing a urinary incontinence pad comprising a tubular pad having an absorbent hollow interior, wherein a first end of the pad is closed and a second end of the pad is open;
   spreading a first side of a channel disposed on a front side of the tubular pad from a second side of the channel, wherein the first and second sides are biased toward each other;
   placing the first and second sides over a labia minora of the user, such that the first and second sides are secured between the labia minor and a labia majora of the user;
   aligning the first end of the pad with a clitoris, such that the tubular pad is prevented from sliding thereby;
   positioning the first end over a urethral meatus of the user, such that urine expelled therefrom is received within the hollow interior;
   releasing the first and second sides to removably secure the tubular pad to the user.

5. The urinary incontinence pad of claim 1, wherein the tubular pad is tapered toward the closed first end.

6. The urinary incontinence pad of claim 1, wherein the closed first end is rounded.

7. The urinary incontinence pad of claim 1, wherein the tubular pad is composed of an absorbent material.

8. The urinary incontinence pad of claim 1, further comprising an outer layer disposed on an exterior of the tubular pad, wherein the outer layer is composed of a liquid impermeable material.

9. The urinary incontinence pad of claim 1, wherein the channel is tapered toward the closed first end of the tubular pad.

10. The urinary incontinence pad of claim 2, wherein the tubular pad is tapered toward the closed first end.

11. The urinary incontinence pad of claim 2, wherein the closed first end is rounded.

12. The urinary incontinence pad of claim 2, wherein the tubular pad is composed of an absorbent material.

13. The urinary incontinence pad of claim 2, further comprising an outer layer disposed on an exterior of the tubular pad, wherein the outer layer is composed of a liquid impermeable material.

14. The urinary incontinence pad of claim 2, wherein the channel is tapered toward the closed first end of the tubular pad.

15. The urinary incontinence pad of claim 3, wherein the tubular pad is tapered toward the closed first end.

16. The urinary incontinence pad of claim 3, wherein the closed first end is rounded.

17. The urinary incontinence pad of claim 3, wherein the tubular pad is composed of an absorbent material.

18. The urinary incontinence pad of claim 3, further comprising an outer layer disposed on an exterior of the tubular pad, wherein the outer layer is composed of a liquid impermeable material.

\* \* \* \* \*